United States Patent [19]

Coenen et al.

[11] Patent Number: 4,925,651
[45] Date of Patent: May 15, 1990

[54] RADIOFLUORO-TYROSINE DERIVATIVES, THE PREPARATION AND USE THEREOF

[75] Inventors: Heinz H. Coenen, Grevenbroich; Peer Kling, Aldenhoven; Gerhard Stoecklin, Titz-Kalrath, all of Fed. Rep. of Germany

[73] Assignee: Kernforschungsanlage Juelich Gesellschaft mit beschrankter Haftung, Juelich, Fed. Rep. of Germany

[21] Appl. No.: 280,804

[22] Filed: Dec. 7, 1988

[30] Foreign Application Priority Data

Jan. 8, 1988 [DE] Fed. Rep. of Germany ....... 3800302

[51] Int. Cl.$^5$ ..................... A61K 49/02; C07C 101/72
[52] U.S. Cl. ..................................... 424/1.1; 562/445
[58] Field of Search ........................... 424/1.1; 562/445

[56] References Cited

U.S. PATENT DOCUMENTS 4,469,680 9/1984 Huffman et al. ................. 424/1.1 X
4,695,449 9/1987 Pawelek ............................. 424/1.1

FOREIGN PATENT DOCUMENTS 1391918 4/1975 United Kingdom .

OTHER PUBLICATIONS

Bustany et al., "Protein Synthesis Evaluation in Brain and Other Organs in Human by PET." Positron Emission Tomography, Dreivich et al. eds, Alan R. Liss, Inc. (1985) pp. 183–201.
Coenen et al., "Synthesis, Autoradiography and Biochemistry of L-$^{18}$F-Fluorophenylalanines for Probing Protein Synthesis," Nuklear medizin, suppl. 22 (1986) pp. 600–602.
Chirakal et al., "Synthesis of 2- and 3-Fluorotyrosine with Dilute Fluorine Gas," Journal of Fluorine Chemistry, vol. 37 (1987) pp. 267–278.
Wagner, J. Nucl. Med., 29(8)1329–1331 (Aug. 1988).

Primary Examiner—John S. Maples
Attorney, Agent, or Firm—Foley & Lardner, Schwartz, Jeffery, Schwaab, Mack, Blumenthal & Evans

[57] ABSTRACT

The use of 2-radiohalogenotyrosine derivatives of the formula I

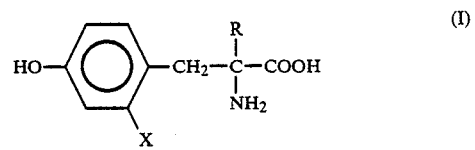

in which X denotes a radioactive halogen, in particular fluorine-18, bromine-75 or iodine-123, and R denotes hydrogen or methyl, in particular of 2-fluoro(18)-tyrosine and -methyltyrosine (II) for emission-tomographic measurement of protein synthesis in vivo, in particular for the purposes of cerebral diagnosis, by means of SPECT and, in particular, by means of PET, provides, in view of the particularly high incorporation rate, especially of II, the possibility of quantitative kinetic evaluation and is thus of great interest, specifically in the framework of tumor diagnosis.

5 Claims, No Drawings

RADIOFLUORO-TYROSINE DERIVATIVES, THE PREPARATION AND USE THEREOF

DESCRIPTION

The invention relates to radiohalogenotyrosine derivatives and to the preparation and use thereof as radiopharmaceuticals.

Modern medical diagnostic methods, such as emission tomography, make it possible to establish the presence of pathological changes non-invasively. This is based on the measurement of biochemical functions using radioactive, labeled—especially with short-lived positron emitters—tracers in vivo.

One of the most important biochemical processes apart from energy metabolism is protein synthesis, which takes place in all tissues. This is why there is a number of approaches to the development of labeled amino acids for the external measurement of protein synthesis in humans. Used almost exclusively for this to date have been natural amino acids labeled with carbon-11 ($T_{\frac{1}{2}}=20$ min) for positron emission tomography Chosen for this have been essential neutral acids which exhibit high brain extraction (see Bustany et al. "Positron Emission Tomography" Alan R. Liss, Inc. 1985, pages 183–201). Known examples are L-[1-$^{11}$C]-leucine, L-[5-$^{11}$C]-methionine and L-[1-$^{11}$C]-tyrosine which have already been used for the measurement of protein synthesis in various diseases of the brain.

A disadvantage associated with the use of $^{11}$C-labeled compounds is, on the one hand, the relatively short half-life of $^{11}$C compared with protein synthesis, which takes more than 60 min in the brain for example, and, on the other hand, all natural amino acids are involved in a number of other metabolic processes besides their use as building block of proteins.

Thus, the labeling atom is rapidly eliminated as $^{11}$CO$_2$ from C$_1$-labeled amino acids. Hence it was possible to draw up a model for the quantitative determination of the rate of protein synthesis for, for example, [$^{11}$C]-leucine only by making simplifying assumptions and taking a fourth compartment into account, which makes the calculation very complicated.

Methionine is also used in the body for methylation, and tyrosine is, in particular, a precursor of catecholamines and thyroid hormones. Thus, it is possible in these cases too to expect reutilization and redistribution of the label in the form of various metabolites, some of which are formed in the liver. This has been demonstrated, for example, for [5-$^{11}$C]-methionine which, nevertheless, is currently the best tracer used, in particular, for measuring metabolic tumor activity.

Furthermore, neutral amino acids use the same transport system in the brain (blood-cell), and it has recently been established that the total net transport of these compounds into the brain is negligibly small.

This is why a number of radiolabeled halogenated amino acids have been prepared and their physiological behavior has been investigated. Chosen for this were, in particular, aromatic amino acids fluorinated in the nucleus, specifically fluorinated phenylalanines. Furthermore, German Pat. No. 2,145,282 describes 1-(iodohydroxyphenyl)-2-aminopropane derivatives radiolabeled in the 3-position with iodine and intended for use for tumor and adrenal diagnostic methods. Also mentioned is, inter alia, 3-iodo-α-methyltyrosine.

Investigations by Coenen et al. (Nuklearmedizin Suppl. 22, (1986) pages 600 to 602) with p-[$^{18}$F]-fluorophenylalanine demonstrated its acceptance for cerebral protein synthesis, but the incorporation rate of this molecule is relatively low and, in the animal model, about 20% of the radioactivity in cerebral tissue had to be assigned to an unidentified metabolite pool. Similar incorporation rates are shown by other 2-, 3- and 4-radiohalogen-substituted phenylalanines, and by tyrosines substituted in the 3-position.

Surprisingly, tyrosines halogenated in the 2-position now show a particularly high incorporation rate.

Hence the invention relates to 2-radiohalogenotyrosine derivatives of the formula I

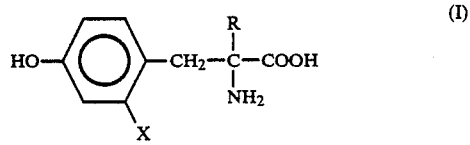

in which X denotes a radioactive halogen, in particular fluorine-18, bromine-75 or iodine-123, and R denotes hydrogen or methyl.

2-Radiohalogenotyrosine derivatives of this formula I are obtained in a manner known per se when a compound of the formula II

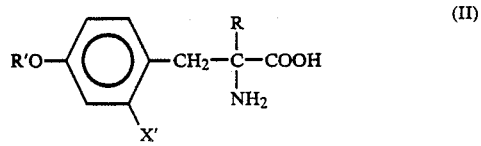

in which R denotes hydrogen or methyl, and R' denotes an esterifying acyl group, is, in a manner known per se, subjected either to electrophilic substitution with an electrophilic radioactive species of the halogen to be introduced into the 2-position, when X' denotes hydrogen or an organometallic radical, (with addition, where appropriate, of an oxidizing agent if radiobromide or radioiodide is used) or to halogen exchange with the desired radiohalide, when X' denotes halogen, followed by hydrolytic elimination of the acyl group and then isolation by chromatography of the compound of the formula I which is formed.

This is because it has been established that 2-halogen-substituted tyrosines are, astonishingly, incorporated considerably more rapidly than the analogous compounds substituted in the 3-position. Thus, for example, the cerebral incorporation rate measured with 2-[$^{18}$F]-fluorotyrosine after 40 min was comparable to that for the natural amino acids methionine and phenylalanine, i.e. the new labeled compounds are comparable to the $^{11}$C-labeled compounds in terms of the incorporation rate. However, they have the additional advantage that the abovementioned problems in evaluation due to additional metabolic processes do not apply:

A detailed investigation has shown that the radioactivity in tissue up to two hours after injection of 2-[$^{18}$F]-fluorotyrosine is distributed only over the free fluorinated amino acid and the portion incorporated in protein.

An influence from redistributed labeled metabolites from the blood can be ruled out. Appropriate analysis in the striatum, the area of the brain which is highly permeated by dopaminergic nerve cells, has also ruled out the formation of catecholamines from 2-fluorotyrosine.

Thus 2-[$^{18}$F]-fluorotyrosine is an ideal tracer for the quantification of the rate of protein synthesis using a three-compartment model, which is relatively easy to handle mathematically and as is used for 2-[$^{18}$F]-fluorodeoxyglucose in PET studies. The uptake of >1.6% of the injected dose per gram of tissue (see table below) is, moreover, adequate for PET investigations. Preliminary experiments with analogs labeled with iodine-123 in rats which had undergone implantation of myeloma tumor cells showed higher incorporation in tumors relative to normal tissue, which makes it probable that this tracer is suitable for diagnosing tumors and metastases.

The water-soluble compounds of the invention are expediently used in a physiological saline solution (NaCl) for injection. Sterilization before use is carried out by sterile filtration through Millipore filters.

Examples illustrating the invention follow.

EXAMPLE 1

50 μmol of L-O-acetyltyrosine were dissolved in about 5 ml of trifluoroacetic acid. Gaseous fluorine labeled with fluorine-18 was passed into the solution at 0° C. (max. 45 μmol; in 0.2% concentration in neon). [$^{18}$F]-F$_2$ was produced by the $^{20}$Ne(d,α)$^{18}$F nuclear reaction in a nickel target, which contained 0.2% F$_2$ in neon (18 bar), by irradiation with 14 MeV deuterons (15 μA).

After the F$_2$/Ne gas mixture had been passed through, the solvent was evaporated off, and the residue was digested with 0.5 mmol of NaOH in 2 ml of water for 10 minutes to eliminate the acetyl group. After neutralization, the solution was fractionated by high-pressure liquid chromatography (HPLC), and the product 2-[$^{18}$F]-fluorotyrosine was isolated. Used for this were preparative reverse-phase columns (250×16 mm) packed with Nucleosil C-18. The eluent used was water: methanol: acetic acid (100:5:1) or 0.035 M sodium citrate/HCl buffer at pH 2.7: isopropanol:dodecyl sulfate (90:10 0.1; VVW). The k' values of 2- and 3- fluorotyrosine are 3.3 and 2.9, and 11.3 and 8.2, respectively. When dodecyl sulfate was used it was removed by filtration through a Dowex anion exchanger (60×10 mm) in the Cl$^-$ form, with the fluorotyrosine being eluted with water. After the eluted solutions had been evaporated to dryness, the product was taken up in isotonic NaCl solution.

The radiochemical yield of L-2-[$^{18}$F]-tyrosine was 17%, and that of the 3-isomer was 3%, with specific activities of about 50 GBq/mmol. The optical configuration (L-form) of the derivatives remains unchanged in the fluorination and working up.

EXAMPLE 2

Typically, 0.75 to 1.5 MBq of L-2-[$^{18}$F]-fluorotyrosine in 50 to 100 μl of isotonic solution were injected into the tail vein of NMRI mice.

After a defined incubation time, the animals were sacrificed and the brains were removed within 20 s and frozen in liquid nitrogen. Parts of the frontal cortex were removed (about 20 mg), weighed, homogenized in distilled water by ultrasonic treatment and, after 10 s, trichloroacetic acid (TCA) was added (final concentration >10%). The protein fraction precipitated by TCA was spun down and washed 2× with TCA solution, and the radioactivity in the combined supernatants and in the protein pellet was measured. The fraction incorporated in cerebral proteins was, for example, 44±3% after 20 min and 84±% after 60 min, i.e. incorporation is almost quantitative >1 h after the injection.

The supernatant was investigated by HPLC (for conditions, see Example 1) for the proportion of free 2-[$^{18}$F]-fluorotyrosine. It emerged from this that the activity not incorporated in proteins was present almost entirely as unmetabolized 2-fluorotyrosine. For example, the measurements were 51±3% at 20 min and 11±2% at 60 min, of the total tissue activity; i.e. recovery of the activity was almost quantitative, being 95±6% and 95±4%, respectively. This means that 2-[$^{18}$F]-fluorotyrosine is present in brain tissue virtually only in two chemical forms.

Results of comparative experiments on the incorporation of halogenated amino acids in mouse brain (40 min after i.v. injection) are compiled in the table which follows:

| Amino acid | Uptake % of inj. dose/g | Incorporation, % of cerebral activity |
|---|---|---|
| 2 - $^{18}$FPhe | 2.0 ± 0.4 | 11 ± 2 |
| 4 - $^{18}$FPhe | 1.5 ± 0.3 | 20 ± 2 |
| 2 - $^{18}$FTyr | 1.3 ± 0.005 | 62 ± 3 |
| 3 - $^{18}$FTyr | 0.8 ± 0.005 | 26 ± 1 |
| 2 - $^{75}$BrPhe | 2.4 ± 0.4 | 15 ± 1 |
| 4 - $^{75}$BrPhe | 2.0 ± 0.4 | 17 ± 5 |
| 3 - $^{123}$ITyr | 0.2 ± 0.005 | 13 ± 4 |
| 3 - $^{123}$I-α-MeTyr | 0.8 ± 0.1 | 18 ± 1 |
| $^{14}$C-Phe | — | 63 ± 2 * |
| $^{14}$C-Leu | — | 85 ± 4 * |
| $^{14}$C-Met | — | 57 ± 3 * |

*Literature data.

This demonstrates the outstanding utility of 2-[$^{18}$F]-fluorotyrosine.

This demonstrates the outstanding utility of 2-[$^{18}$F]-fluorotyrosine.

We claim:

1. Substantially pure 2-[$^{18}$F]-fluoro-a-methyltyrosine.

2. In a method of emission-tomographically measuring protein synthesis in vivo by positron emission tomography or single photon emission tomography, the improvement comprising administering an amount, effective as a radio- tracer, of 2-[$^{18}$F]-fluorotyrosine or 2-[$^{18}$F]-fluoro-a-methyltyrosine.

3. The method of claim 2, wherein said compound is 2-[$^{18}$F]-fluorotyrosine.

4. The method of claim 2, wherein said compound is 2-[$^{18}$F]-fluoro-α-methyltyrosine.

5. The method of claim 2, wherein said protein synthesis is measured in the brain.

* * * * *